United States Patent [19]

Shinozaki et al.

[11] Patent Number: 5,212,042

[45] Date of Patent: May 18, 1993

[54] POSITIVE TYPE LIGHT-SENSITIVE COMPOSITION

[75] Inventors: Fumiaki Shinozaki; Akira Umehara; Sadao Ishige, all of Shizuoka, Japan

[73] Assignee: Fuji Photo Film Co., Ltd., Kanagawa, Japan

[21] Appl. No.: 844,869

[22] Filed: Mar. 2, 1992

Related U.S. Application Data

[63] Continuation of Ser. No. 570,753, Aug. 22, 1990, abandoned.

[30] Foreign Application Priority Data

Aug. 22, 1989 [JP] Japan .................. 1-215619

[51] Int. Cl.$^5$ ................................................ G03C 1/52
[52] U.S. Cl. ................................. 430/189; 430/191; 430/192
[58] Field of Search .................. 430/189, 192, 191

[56] References Cited

U.S. PATENT DOCUMENTS

| 2,759,817 | 8/1956 | Schmidt et al. | 430/189 |
| 3,050,387 | 8/1962 | Neugebauer et al. | 430/189 |
| 3,050,388 | 8/1962 | Neugebauer et al. | 430/189 |
| 3,567,453 | 3/1971 | Borden | 430/192 |

Primary Examiner—Marion E. McCamish
Assistant Examiner—Kathleen Dudd
Attorney, Agent, or Firm—Sughrue, Mion, Zinn, Macpeak & Seas

[57] ABSTRACT

A positive type light-sensitive composition is disclosed, comprising an alkali-soluble high-molecular binder and at least one p-iminoquinonediazido-N-sulfonyl compound. This composition can be used for forming a resist for an IC board, a printing plate, a silver-free, image-forming material, etc.

4 Claims, No Drawings

POSITIVE TYPE LIGHT-SENSITIVE COMPOSITION

This is a continuation of application Ser. No. 07/570,753, filed Aug. 22, 1990, now abandoned.

FIELD OF THE INVENTION

This invention relates to a positive type, light-sensitive composition which can be used for forming resists having a micropattern for IC base boards, printing plates or silver-free, image-forming materials.

BACKGROUND OF THE INVENTION

Resist compositions have encountered a new limitation in the field of very small electronic parts. The requirement for producing etched structures of a microscopic dimension on a large scale leads to a demand for those resists which have a higher sensitivity to actinic radiation, which provide a higher contrast, which possess a better spectral sensitivity and, therefore, provide an improved resolving power and a broader processing allowance, and which servo to reduce the unit cost of final electronic devices.

One useful positive type light-sensitive composition contains a polymer having repeating units with photosensitive pendant quinonediazido groups and a monomer which may insolubilize the polymer, where the quinonediazido groups have not undergone decomposition by exposure to actinic radiation. One function of such a monomer is to impart some thermal resistance to the composition by its thermal conversion to a ketene and subsequent cross linking. For example, U.S. Pat. No. 4,365,019 describes 1,3,5-trihydroxybenzene esterified with 1,2-naphthoquinonediazidosulfonic acid as the monomer. A particularly useful polymer is the so-called novolak resin. The image/non-image difference in a diazoketone/novolak photoresist system is determined by the principle of solution inhibition. This diazoketone/novolak system positive type photoresist usually functions very well, but is still insufficient because 1,2-naphthoquinonediazide light-sensitive substances have conventionally been known to be difficult to shift their sensitive wavelength and to spectrally sensitize, and they therefore have been limited as to their application as both resist materials and printing materials such as printing plates.

SUMMARY OF THE INVENTION

An object of the present invention is to provide a novel positive type light-sensitive composition which has a higher sensitivity and provides more contrast and which can be spectrally sensitized, thus replacing the conventional naphthoquinonediazide/novolak resin system.

This and other objects of the present invention will become apparent from the following description thereof.

The above-described and other objects of the present invention are attained by a positive type light-sensitive composition, which contains an alkali-soluble polymeric binder and at least one p-iminoquinonediazido-N-sulfonyl compound. The positive type light-sensitive composition may further comprise a dye-borate complex represented by the formula (II):

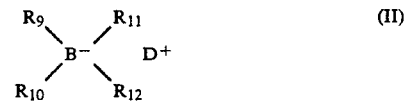

wherein $D^+$ represents a cation dye, and $R_9$, $R_{10}$, $R_{11}$ and $R_{12}$ each independently represents an alkyl group, a substituted alkyl group, an aryl group, a substituted aryl group, an aralkyl group, a substituted aralkyl group, an alkaryl group, a substituted alkaryl group, an alkenyl group, a substituted alkenyl group, an alicyclic group, a substituted alicyclic group or a heterocyclic group.

DETAILED DESCRIPTION OF THE INVENTION

The application of p-iminoquinonediazide compounds to an image-forming process has been investigated since Sus. O presented the following photo-reaction in *Just us Liebigs Ann. Chem.*, 598, pp. 123–138 (1956).

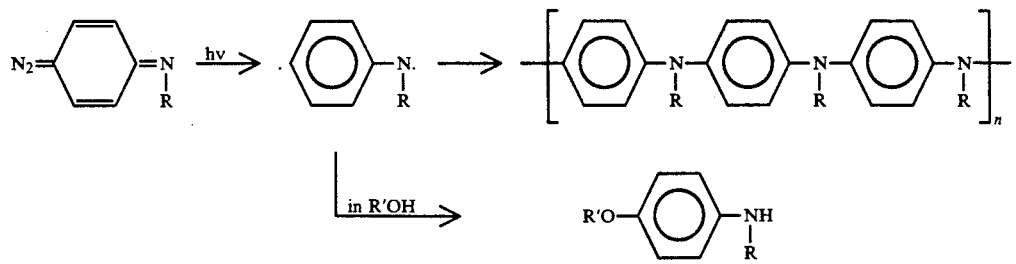

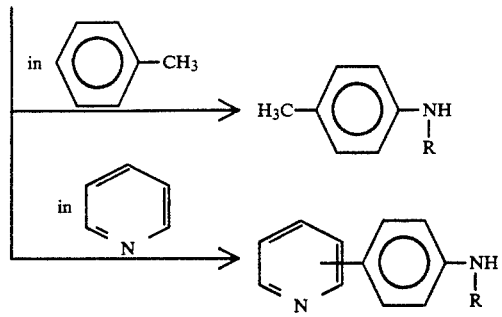

Examples of the application of this reaction to image formation are disclosed, for example, in U.S. Pat. Nos. 2,759,817, 3,175,906, 3,180,732, 3,050,388 and 3,676,134, JP-B-47-12643 (The term "JP-B" as used herein means an "examined Japanese patent publication") (corresponding to U.S. Pat. No. 3,709,956) and JP-B-49-14884. However, all of these relate to the formation of negative images, and nothing is described therein on the formation of positive images.

This may be attributed to the fact that, as is described in the above-mentioned specifications, the p-iminoquinonediazide compound is used in a larger weight proportion than the polymeric binder in the light-sensitive composition comprising the polymeric binder and the p-iminoquinonediazide.

The inventors of the present invention have found that a high contrast positive image can surprisingly be obtained by using a light-sensitive composition wherein a p-iminoquinonediazide is used in an alkali-soluble polymeric binder such as a phenol resin in a weight ratio of binder/p-iminoquinonediazide of about 1/0.1 to about 1/0.7, preferably about 1/0.15 to about 1/0.5, and imagewise exposing and developing the composition with an alkaline aqueous solution.

The various p-iminoquinone diazido compounds disclosed in the foregoing specifications can be used as the p-iminoquinonediazide in the present invention, with p-iminoquinonediazido-N-sulfonyl compounds represented by the following formula (I) being particularly preferred:

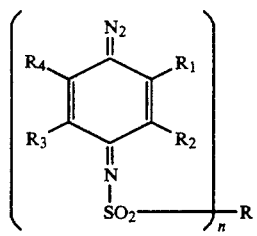 (I)

wherein $R_1$, $R_2$, $R_3$ and $R_4$ each independently represents a hydrogen atom, a halogen atom (e.g., fluorine atom, chlorine atom, bromine atom and iodine atom), an alkyl group, a substituted alkyl group, an alkoxy group, a substituted alkoxy group, an aralkyl group, a substituted aralkyl group, an alkaryl group, a substituted alkenyl group, a cyano group, a heterocyclic group,

(wherein $R_5$ and $R_6$ each independently represents a hydrogen atom, an alkyl group, a substituted alkyl group, an aralkyl group, a substituted aralkyl group, an alkenyl group, a substituted alkenyl group, an aryl group, a substituted aryl group or, when taken together, $R_5$ and $R_6$ represent the atoms necessary for forming a heterocyclic ring) or

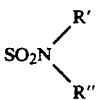

(wherein $R_7$ represents a hydrogen atom, an alkyl group or a substituted alkyl group, and $R_8$ represents an alkyl group, a substituted alkyl group, an aryl group, a substituted aryl group, an aralkyl group, a substituted aralkyl group, an alkenyl group or a substituted alkenyl group), provided that $R_1$ and $R_2$ and/or $R_3$ and $R_4$ may constitute one or two fused carbon ring(s) or heterocyclic ring(s), and R represents an aryl group, a substituted aryl group, an aralkyl group, a substituted aralkyl group, an alkenyl group or a substituted alkenyl group.

In the definitions for $R_1$, $R_2$, $R_3$ and $R_4$, the unsubstituted or substituted alkyl group or the unsubstituted or substituted alkoxy group preferably contains 1 to 15 carbon atoms, and the unsubstituted or substituted aralkyl group preferably contains 6 to 15 carbon atoms.

Specific examples of the substituent which may substitute for the alkyl group, the alkoxy group, the aralkyl group, the alkenyl group or the aryl group in the definitions for $R_1$, $R_2$, $R_3$, $R_4$, $R_5$, $R_6$, $R_7$ and $R_8$ include a halogen atom, an aryl group, the group $$-SO_2N\begin{matrix}R'\\R''\end{matrix}$$

or a heterocyclic ring.

Specific examples of the p-iminoquinonediazido-N-sulfonyl compounds of the present invention are illustrated below. However, these examples are not to be construed as limiting the present invention in any way.

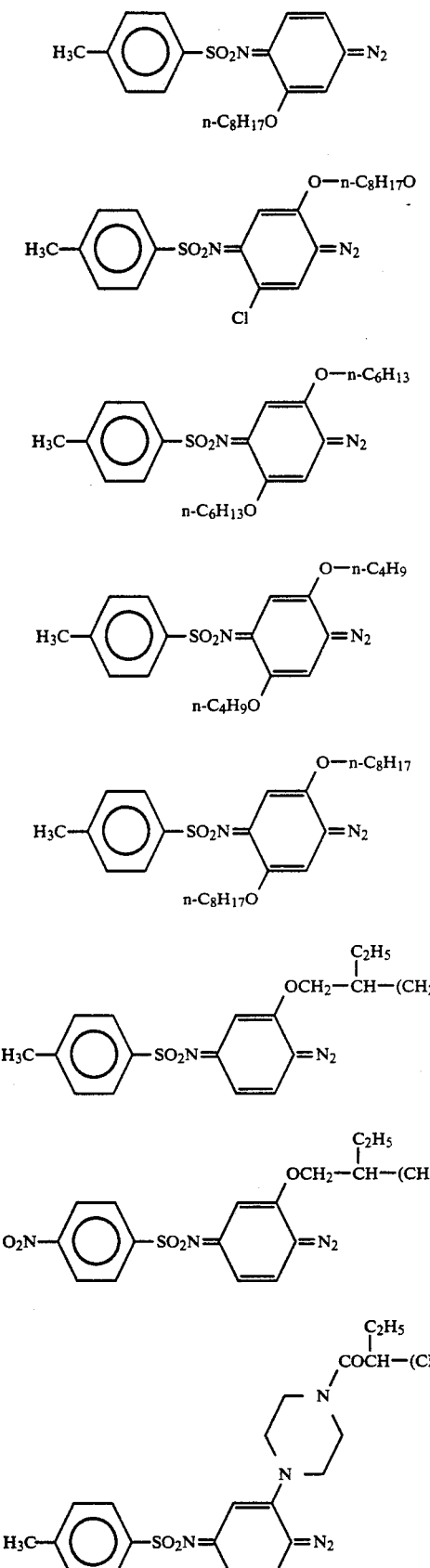

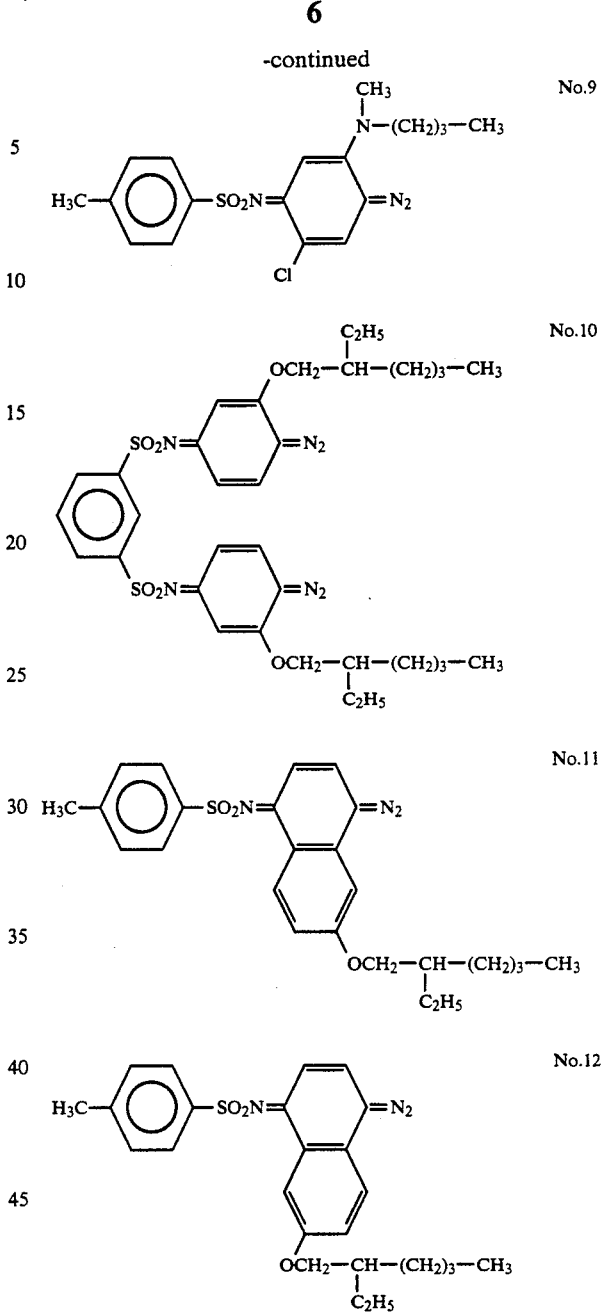

The positive type light-sensitive composition of the present invention is essentially constituted by an alkali-soluble binder and the aforesaid p-iminoquinonediazide compound, and may it optionally contain, if necessary, other additives such as a stabilizer, a surface active agent, a development accelerator disclosed in U.S. Pat. No. 4,365,019, a printing-out agent, etc. Further, spectrally sensitizing agents to be described hereinafter may also be added thereto.

Useful polymeric binders are exemplified by a phenolformaldehyde resin and other phenolic polymers. Particularly preferred examples of the binder include well-known novolak resins, that is, resins represented by the following structural formula:

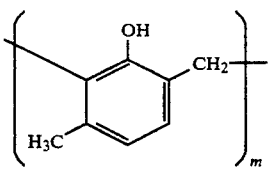

wherein m is an integer of from 2 to 20, preferably from 3 to 15.

Other phenolic polymers useful in the present invention are polyvinylphenol, poly(p-hydroxystyrene) and poly(hydroxydiphenylmaleimide).

Other binders to be preferably used in the present invention include those which contain repeating units of polysulfonamide group, copolymers of acrylate or methacrylate copolymerized with acrylic acid or methacrylic acid, and those which are described in U.S. Pat. No. 4,141,733.

In the composition of the present invention, various conventional iminoquinonediazido-N-sulfonyl compounds may be used as a mixture or together with conventional 1,2-naphthoquinone-diazido compounds.

Spectral sensitization of the positive type light-sensitive composition of the present invention is described below. The p-iminoquinonediazide compounds can effectively be spectrally sensitized with a cationic dye/borate anion complex represented by the following formula (II):

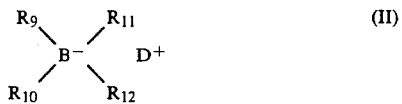

wherein $D^+$ represents a cationic dye, and $R_9$, $R_{10}$, $R_{11}$ and $R_{12}$ each independently represents an alkyl group, a substituted alkyl group, an aryl group, a substituted aryl group, an aralkyl group, a substituted aralkyl group, an alkaryl group, a substituted alkaryl group, an alkenyl group, a substituted alkenyl group, an alicyclic group, a substituted alicyclic group or a heterocyclic group.

The dye complex is used in an amount preferably 0.05 to 0.7 part by weight, preferably 0.1 to 0.5 part by weight, per 1 part by weight of the p-imino-quinonediazide compound and, where the complex is used in a smaller amount within the above-described range, a borate salt (e.g., quaternary ammonium salt) is preferably added in an excess amount up to about three times as much as the amount of the complex.

The light-sensitive composition of the present invention may preferably be mixed into an organic solvent or dissolved into the organic solvents by means of an ultrasonic wave and preferably subjected filtration, and then, coated onto a proper support by means of rotary coating, roll coater coating, dip coating and the like, followed by drying at a temperature of from room temperature to 120° C., and thereafter imagewise exposed to an activating radiation such as light or an electron beam radiation in a contact manner or in a projection manner.

Useful supports include sheets or foils of metals such as aluminum, copper, magnesium or zinc; glass or glass covered by a metal such as chromium, chromium alloy, steel, silver, gold or platinum; and film bases of synthetic polymeric materials such as poly(alkyl methacrylate)(e.g., poly(methyl methacrylate)), polyesters (e.g., poly(ethylene terephthalate)), poly(vinyl acetal), polyamides, nylon, and cellulose ester films (e.g., cellulose nitrate, cellulose acetate, cellulose acetate propionate, cellulose acetate butyrate, etc.). In the production of IC devices, silicon or silicon dioxide wafers and silicon nitride or chromium-covered glass plate supports are particularly useful. In some cases, an adhesion aid may first be coated as an undercoat depending upon the kind of support selected.

A proper solvent to be used for preparing a coating solution of the light-sensitive composition may be selected from among common coating solvents. Useful solvents include, for example, an alcohol, an ester, an ether and a ketone, and specific examples thereof include 2-ethoxyethanol acetate, n-butyl acetate, 4-butyrolactone and a mixture thereof being preferred.

The final thickness of the coated film varies depending upon the end use and the kind of etching agent (if used). A preferred thickness falls within the range of, for example, from about 0.5 to about 20 μm.

The pre-baking and post-baking techniques described in U.S. Pat. No. 4,141,733 are preferable in the present invention.

A conventional exposing apparatus may be used for the imagewise exposure. The exposing time varies depending upon various factors, but is preferably in the range of from about 6 seconds to about 90 seconds. The composition of the present invention shows a markedly improved sensitivity to activating radiation in comparison with conventional resist compositions.

After the imagewise exposure, the light-sensitive composition is developed with a proper alkali developer. Conventional developers for positive development may effectively be used. Those which contain sodium hydroxide or sodium phosphate, those which are described in U.S. Pat. No. 4,141,733 and EP-A-23758, i.e., those which contain a sulfite-stabilizing agent and a quaternary alkanolammonium hydroxide are particularly preferred.

The present invention is now illustrated in greater detail by reference to the following examples. However, these examples are not to be construed as limiting the present invention in any way. Unless otherwise indicated, all parts, percents, and ratios are by weight.

SYNTHESIS EXAMPLE 1

Synthesis of 1-[(p-toluenesulfonyl)imino]-2-(n-octyloxy)benzoquinone-(1,4)-diazide-(4) (Compound No. 1)

2-Hydroxy-4-nitroacetanilide was reacted with n-octyl bromide for 3 hours under heating in a solvent of dimethylformamide in the presence of anhydrous potassium carbonate to obtain 2-(n-octyloxy)-4-nitroacetanilide in a yield of 90.7%.

Then, 2-(n-octyloxy)-4-nitroacetanilide was boiled in a hydrocloric acid-methanol solution for 3 hours, followed by neutralization to obtain 2-(n-octyloxy)-4-nitroacetaniline in a yield of 97.7%.

2-(n-octyloxy)-4-nitroacetaniline and p-toluenesulfonium chloride were then boiled in a solvent of acetonitrile for 3 hours over a steam bath using pyridine as an acid-binding agent to obtain 2-(n-octyloxy)-4-nitro-(p-toluenesulfone)anilide in a yield of 94%.

75.6 g of 2-(n-octyloxy)-4-nitro-(p-toluenesulfone)anilide was then gradually added to a mixture of 50.3 g of reduced iron, 2.9 g of ammonium chloride, 18 g of water, 130 ml of isopropyl alcohol and 130 ml of dimethylformamide over a period of about 10 minutes under heating over a steam bath, and the components were reacted for 3 hours under heating over the steam bath. After completion of the reaction, the reaction mixture was diluted with methanol, insoluble components were filtered off, and the filtrate was poured into a large amount of water. The aqueous solution was then extracted with ethyl acetate, and the extract was concentrated to obtain 65 g of 3-(n-octyloxy)-4-(p-toluenesulfonyl)aminoaniline (yield: 92.6%).

Then, 39 g of 3-(n-octyloxy)-4-(p-toluenesulfonyl)aminoaniline was dissolved in a mixed solution of 300 ml of methanol and 25.3 ml of concentrated hydrochloric acid. The solution was cooled to $-10°$ to $-5°$ C., and a solution of 6.9 g of sodium nitrite in 14 ml of water was added thereto in several seconds and, after 10 minutes, 18.5 g of powdery potassium hexafluorophosphate was added thereto. Thereafter, 150 ml of water was dropwise added thereto over about 30 minutes, and the resulting mixture was stirred for about one hour while keeping the internal temperature at about 5° C. 3-(n-Octyloxy)-4-(p-toluene-sulfonyl)aminobenzenediazonium hexafluorophosphate precipitated as crystals was filtered out, and washed with a mixed solvent of methanol-water to obtain 48.4 g of 3-(n-octyloxy)-4-(p-toluenesulfonyl)aminobenzenediazonium hexafluorophosphate.

36 g of the above-described diazonium salt was dissolved in 200 ml of ethyl acetate, 200 ml of 5% aqueous solution of sodium hydrogencarbonate was added thereto and, after shaking the mixture well, the ethyl acetate layer was separated out using a separating funnel, followed by concentration. The concentrate was crystallized with an ethyl acetate-benzene solution to obtain 25.7 g of 1-[p-toluenesulfonyl)imino]-2-(n-octyloxy)-benzoquinone-(1,4)-diazide-(4) (m.p.=114° to 116° C., $\lambda_{max}=390$ nm (solvent: methyl ethyl ketone), yield: 97.4%).

SYNTHESIS EXAMPLE 2

Synthesis of
1-[(p-toluenesulfonyl)imino]-2-chloro-5-(n-octyloxy)-benzoquinone-(1,4)-diazide-(4) (Compound No. 2)

2-Hydroxy-4-nitro-5-chloroacetanilide was reacted with n-octyl bromide in the same manner as the corresponding reaction in Synthesis Example 1 to obtain 2-(n-octyloxy)-4-nitro-5-chloroacetanilide.

25.8 g of this anilide was then gradually added dropwise to a mixture of 22.4 g of reduced iron, 0.13 g of ammonium chloride, 14.4 g of water and 60 ml of isopropyl alcohol over a period of about 10 minutes under heating over a steam bath, and the components were reacted for 3 hours under heating over the steam bath. After completion of the reaction, the reaction mixture was diluted with methanol, insoluble components were filtered off, and the filtrate was poured into a large amount of water. The aqueous solution was then extracted with ethyl acetate, and the extract was concentrated to obtain 21.7 g of 2-chloro-4-acetamino-5-(n-octyloxy)aniline (yield: 93%).

Then, the resulting aniline was reacted with p-toluenesulfonyl chloride in a conventional manner to obtain 34 g of 2-chloro-4-acetamido-5-(n-octyloxy)-p-toluenesulfone)anilide. This compound was added to a mixed solution of 80 ml of methanol and 24 ml of concentrated hydrochloric acid, and the mixture was boiled for 3 hours and then neutralized to obtain 18.4 g of 2-(n-octyloxy)-4-(p-toluenesulfonyl)amino-5-chloroaniline.

Then, the above-described aniline was diazotized in the same manner as the corresponding reaction in Synthesis Example 1 and then neutralized with sodium hydrogencarbonate to obtain 15.1 g of 1-[(p-toluenesulfonyl)imino]-2-chloro-5-(n-octyloxy)benzoquinone-(1,4)-diazide-(4). (m.p.=125° to 127° C.; $\lambda_{max}=378$ nm (solvent: methyl ethyl ketone)).

SYNTHESIS EXAMPLE 3

Synthesis of
1-[(p-toluenesulfonyl)imino]-2,5-di(n-hexyloxy)benzoquinone-(1,4)-diazide-(4) (Compound No. 3)

11.6 g of 1,4-di(n-hexyloxy)benzene was dissolved in a mixed solvent of 50 ml of acetic anhydride and 50 ml of n-hexane, and 4 ml of concentrated nitric acid having a specific gravity of 1.42 was dropwise added thereto at a room temperature of 20° C. over 3 minutes. The internal temperature rose to 46° C., and the reaction was completed to obtain 13.1 g of 2,5-di(n-hexyloxy)nitrobenzene (yield: 97%).

This nitro compound was reduced to 2,5-(n-hexyloxy)aniline in a conventional manner, and then reacted with p-toluenesulfonyl chloride to obtain 17.5 g of 2,5-di(n-hexyloxy)-(p-toluenesulfone)anilide. Further, this anilide was dissolved in a mixture of 40 ml of acetic anhydride and 40 ml of n-hexane, and 3.7 ml of concentrated nitric acid having a specific gravity of 1.42 was dropwise added to the solution at a room temperature of 20° C. over about 5 minutes. After reacting for 3 hours, the reaction mixture was poured into water and subjected to extraction with benzene, and the extract was concentrated to crystallize it. Thus, 8.9 g of 2,5-di(n-hexyloxy)-4-nitro-(p-toluenesulfone)anilide was obtained.

This nitro compound was then reacted with reduced iron in the same manner as the corresponding reaction in Synthesis Example 1 to obtain 7.6 g of 2,5-di(n-hexyloxy)-4-(p-toluenesulfonyl)aminoaniline. This aniline was diazotized and neutralized with sodium hydrogencarbonate in the same manner as the corresponding reactions in Synthesis Example 1 to obtain 5.6 g of 1-[(p-toluenesulfonyl)imino]-2,5-di(n-hexyloxy)benzoquinone-(1,4)-diazide-(4) (m.p.=98° to 100° C.; $\lambda_{max}=390$ nm (solvent: methyl ethyl ketone)).

SYNTHESIS EXAMPLE 4

Synthesis of
1-[(p-toluenesulfonyl)imino]-2,5-di(n-butoxy)benzoquinone-(1,4)-diazide-(4) (Compound No. 4):

1,4-Di-(n-butoxy)benzene was nitrated, reduced, p-toluenesulfonated, again nitrated, reduced, diazotized and treated with sodium hydrogencarbonate in the same manner as in Synthesis Example 3 to obtain 1-[(p-toluenesulfonyl)imino]-2,5-di(n-butoxy)-benzoquinone-(1,4)-diazide-(4) (m.p.=130° to 132° C.; $\lambda_{max}=388$ nm (solvent: methyl ethyl ketone)).

SYNTHESIS EXAMPLE 5

Synthesis of
1-[(p-toluenesulfonyl)imino]-2,5-di(n-octyloxy)benzoquinone-(1,4)-diazide-(4) (Compound No. 5)

1,4-Di(n-octyloxy)benzene was reacted in the same manner as in Synthesis Example 3 to obtain 1-[(p-toluenesulfonyl)imino]-2,5-di(n-octyloxy)-benzoquinone-(1,4)-diazide-(4) (m.p.=100° to 102° C.; $\lambda_{max}$=390 nm (solvent: methyl ethyl ketone)).

SYNTHESIS EXAMPLE 6

Synthesis of 1-[(p-toluenesulfonyl)imino]-3-(2-ethylhexyloxy)-benzoquinone-(1,4)-diazide-(4) (Compound No. 6)

2-Hydroxy-4-nitroacetanilide was reacted with 2-(ethylhexyloxy)-4-nitroacetanilide for 3 hours in a solvent of dimethylformamide over a steam bath in the presence of anhydrous potassium carbonate to obtain 2-(2-ethylhexyloxy)-4-nitroacetanilide. This nitro compound was reduced with reduced iron in the same manner as the corresponding reaction in Example 1 to obtain 3-(2-ethylhexyloxy)-4-acetaminoaniline. This aniline compound was reacted with p-toluenesulfonyl chloride to obtain 3-(2-ethyl-hexyloxy)-4-acetamino-(p-toluenesulfone)anilide. This anilide compound was boiled in a methanol-hydrochloric acid solution for 3 hours and then neutralized to obtain 3-(2-ethylhexyloxy)-4-(p-toluene-sulfonyl)aminoaniline.

Then, the above-described aniline compound was diazotized in the same manner as in Synthesis Example 1 and then treated with sodium hydrogencarbonate to obtain 1-[(p-toluenesulfonyl)imino]-3-(2-ethylhexyloxy)-benzoquinone(1,4)-diazide-(4) (m.p.=79° to 81° C., $\lambda_{max}$=380 nm (solvent: methyl ethyl ketone)).

SYNTHESIS EXAMPLE 7

Synthesis of 1-[(p-nitrobenzenesulfonyl)imino]-3-(2-ethylhexyloxy)-benzoquinone-(1,4)-diazide-(4) (Compound No. 7)

3-(2-Ethylhexyloxy)-4-acetaminoaniline obtained in Synthesis Example 6 was reacted with p-nitrobenzenesulfonyl chloride to obtain (3-(2-ethylhexyloxy)-4-acetamino-(p-nitrobenzenesulfon)anilide.

Then, the anilide compound was reacted in the same manner as in Synthesis Example 6 to obtain 1-[p-nitrobenzenesulfonyl)imino]-3-(2-ethylhexyloxy)-benzoquinone-(1,4)-diazide-(4) (m.p.=143° to 145° C.; $\lambda_{max}$=383 nm (solvent: methyl ethyl ketone)).

SYNTHESIS EXAMPLE 8

Synthesis of 1-[(p-toluenesulfonyl)imino]-2-chloro-5-[N-(2-ethylhexanoyl)piperadino]-benzoquinone-(1,4)-diazide-(4) (Compound No. 8)

68 g (0.3 mol) of 2,4,5-Trichloronitrobenzene and 77.4 g (0.9 mol) of piperazine were stirred in 100 ml of a dimethylformamide in the presence of 31 g of anhydrous potassium carbonate for one hour at a room temperature of 25° C. to 40° C. and then for one hour at 70° to 80° C. to obtain 49.5 g of 2-piperazino-4,5-dichloronitrobenzene. This compound was reacted with 2-ethylhexanoyl chloride in a solvent of acetonitrile in the presence of pyridine to obtain 2-[N-(2-hexanoyl)-piperazino]-4,5-dichloronitrobenzene.

Then, 50.5 g of the nitrobenzene compound, 25.8 g of p-toluenesulfonamide, and 20.8 g of anyhydrous potassium carbonate were reacted with each other in 40 ml of dimethylacetamide in the presence of 0.3 g of copper powder at 170° to 175° C. for 13 hours and then subjected to column chromatography to obtain 17.7 g of 2-[N-(2-hexanoyl)piperazino]-4-(p-toluenesulfonyl) amino-5-chloro-nitrobenzene.

Subsequently, the nitro group of the compound was reduced to an amino group and then diazotized, followed by treatment with sodium hydrogencarbonate to obtain 1-[(p-toluenesulfonyl)imino]-2-chloro-5-[N-(2-ethyl-hexanoyl)piperazino]-benzoquinone-(1,4)-diazide-(4) (m.p.=132° to 134° C.; $\lambda_{max}$=380 nm (solvent: methyl ethyl ketone)).

SYNTHESIS EXAMPLE 9

Synthesis of 1-[(p-toluenesulfonyl)imino]-2-chloro-5-[N-butyl-N-methyl)amino-benzoquinone-(1,4)-diazide-(4) (Compound No. 9)

The method used in Synthesis Example 8 was used to obtain 1-[(p-toluenesulfonyl)imino]-2-chloro-5-[N-butyl-N-methyl)amino-benzoquinone-(1,4)-diazide-(4) (m.p.=128° to 130° C.; $\lambda_{max}$=367 nm (solvent: methyl ethyl ketone)).

SYNTHESIS EXAMPLE 10

Synthesis of 1-[(m-benzene-disulfonyl)imino]-3-(2-ethylhexyloxy)-benzoquinone-(1,4)-diazide-(4) (Compound No. 10)

3-(2-Ethylhexyloxy)-4-acetaminoaniline obtained in Synthesis Example 6 was reacted with m-benzene-disulfonyl chloride and then deacetylated with a methanol-hydrochloric acid solution to obtain 1,3-bis[4-amino-3-(2-ethylhexyloxy)anilinosulfonyl]-benzene. This compound was diazotized and then treated with sodium hydrogencarbonate to obtain 1-[(m-benzene-disulfonyl)imino]-3-(2-ethylhexyloxy)benzoquinone-(1,4)-diazide-(4) (m.p.=78° to 80° C.; $\lambda_{max}$=381 nm (solvent: methyl ethyl ketone)).

SYNTHESIS EXAMPLE 11

Synthesis of 1-[(p-toluenesulfonyl)imino]-6-(2-ethylhexyloxy)-naphthoquinone-(1,4)-diazide-(4) (Compound No. 11)

81 g of 1-acetamino-7-hydroxy-naphthalene and 85 g of 2-ethylhexyl bromide were reacted with each other in 250 ml of dimethylformamide in the presence of 66.5 g of anhydrous potassium carbonate over a steam bath for 5 hours to obtain 102.4 g of 1-acetamino-7-(2-ethylhexyloxy)naphthalene. This compound was dissolved in a mixed solution of 100 ml of acetic anhydride and 200 ml of glacial acetic acid. 44.2 g of concentrated nitric acid having a specific gravity of 1.42 was dropwise added thereto over about one hour at a temperature of not higher than 10° C., and the components were reacted for about 3 hours at about 10° C. Crystals which precipitated were collected by filtration to obtain 43.5 g of 1-acetamino-4-nitro-7-(2-ethylhexyloxy)naphthalene.

Then, the nitro group of the compound was reduced to an amino group, and the resulting amino compound was reacted with p-toluenesulfonyl chloride and deacetylated to obtain 1-amino-4-(p-toluenesulfonyl)amino-7-(2-ethylhexyloxy)naphthalene.

This naphthalene compound was then diazotized and treated with sodium hydrogencarbonate to obtain 1-[(p-toluenesulfonyl)imino]-6-(2-ethylhexyloxy)-naphthoquinone(1,4)-diazide-(4) (m.p.=134° to 136° C.; $\lambda_{max}$=418 nm (solvent: methyl ethyl ketone)).

SYNTHESIS EXAMPLE 12

Synthesis of 1-[(p-toluenesulfonyl)imino]-7-(2-ethylhexyloxy)naphthoquinone-(1,4)-diazide-(4) (Compound No. 12)

1-Acetamino-4-nitro-7-(2-ethylhexyloxy)naphthalene obtained in Synthesis Example 11 was boiled in a methanolhydrochloric acid solution for 3 hours and then neutralized to obtain 1-amino-4-nitro-7-(2-ethylhexyloxy)naphthalene. This naphthalene was reacted with p-toluenesulfonyl chloride to obtain 1-(p-toluenesulfonyl)amino-4-nitro-7-(2-ethylhexyloxy)naphthalene.

Then, the nitro group of the compound was reduced to an amino group, and the amino group was diazotized, followed by treatment with sodium hydrogencarbonate to obtain 1-[(p-toluenesulfonyl)imino]-7-(2-ethylhexyloxy)-naphthoquinone(1,4)-diazide-(4) (m.p.=132° to 135° C.; $\lambda_{max}$=412 nm (solvent: methyl ethyl ketone)).

EXAMPLES 1–12

The following light-sensitive solution was spin-coated on a 200 μm thick anodized aluminum base and then dried at 100° C. to obtain a 2 μm thick coat.

| | |
|---|---|
| Phenol resin (PR-50904, trade name, made by Sumitomo Dures Co., Ltd.) | 2 g |
| Each Compound obtained in one of Synthesis Examples 1–12 | 0.6 g |
| Methyl ethyl ketone | 15 g |
| Methyl cellosolve acetate | 7 g |

Each of these light-sensitive materials was exposed using an exposing machine for presensitized plates and then developed in an alkali developer for presensitized plates, DP-4 (made by Fuji Photo Film Co., Ltd.), diluted with water in a ratio of 1:8. Light-sensitive materials using the compounds obtained in Synthesis Examples 2 to 12 provided positive images having an extremely high contrast. They showed good inking properties as printing plates.

The light-sensitive material using the compound obtained in Synthesis Example 1 also provided a good positive image. In comparison with the above-described materials, however, it suffered a slight film reduction upon development.

EXAMPLE 13

A coated film of 2 μm in dry thickness was formed in the same manner as in Example 1 except for changing the light-sensitive solution to the following solution.

| | |
|---|---|
| Phenol resin (PR-50904) | 1 g |
| Compound of Synthesis Example 2 | 0.3 g |
| 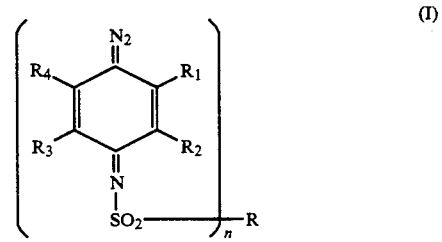 | 0.1 g |
| $(C_6H_5)_3B^-$-n-$C_6H_{13}$ ($\lambda$max: 550 nm) | |
| Methyl ethyl ketone | 7.5 g |
| Methyl cellosolve acetate | 3.5 g |

This light-sensitive material was treated in the same manner as in Example 1 except for using an SC filter transmitting only light having a wavelength longer than 460 nm for the exposure step. A good positive image was obtained.

EXAMPLE 14

A light-sensitive material was prepared in the same manner as in Example 13 except for that the cyanine borate was not added. The material was treated in the same manner as in Example 13. This material did not respond to the light having a wavelength longer than 460 nm.

While the present invention has been described in detail and with reference to specific embodiments thereof, it is apparent to one skilled in the art that various changes and modifications can be made therein without departing form the spirit and the scope of the present invention.

What is claimed is:

1. A positive type light-sensitive composition, comprising an alkali-soluble polymeric binder and at least one p-iminoquinonediazido-N-sulfonyl compound, wherein said at least one p-iminoquinonediazido-N-sulfonyl compound is present in an amount of from 0.1 to 0.7 part by weight per 1 part by weight of said alkali-soluble polymeric binder, and wherein said alkali-soluble polymeric binder is a phenolic polymer.

2. A positive type light-sensitive composition as set forth in claim 1, wherein said at least one p-iminoquinonediazido-N-sulfonyl compound is represented by the following formula (I):

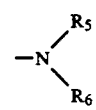

(I)

wherein $R_1$, $R_2$, $R_3$ and $R_4$ each independently represents a hydrogen atom, a halogen atom, an alkyl group, a substituted alkyl group, an alkoxy group, a substituted alkoxy group, an aralkyl group, a substituted aralkyl group, an alkaryl group, a substituted alkaryl group, an alkenyl group, a substituted alkenyl group, a cyano group, a heterocyclic group, $$-N\begin{matrix}R_5\\R_6\end{matrix}$$

(wherein $R_5$ and $R_6$ each represents a hydrogen atom, an alkyl group, a substituted alkyl group, an aralkyl group, a substituted aralkyl group, an alkaryl group, a substituted alkaryl group, an alkenyl group, a substituted alkenyl group, an aryl group, a substituted aryl group or, when taken together, $R_5$ and $R_6$ represent atoms necessary for forming a heterocyclic ring) or $$-SO_2N\begin{matrix}R_7\\R_8\end{matrix}$$

(wherein $R_7$ represents a hydrogen atom, an alkyl group or a substituted alkyl group, and $R_8$ represents an alkyl group, a substituted alkyl group, an aryl group, a substituted aryl group, an aralkyl group, a substituted aralkyl group, an alkaryl group, a substituted alkaryl group, an alkenyl group or a substituted alkenyl group), provided that at least one of $R_1$ and $R_2$ grouped together and $R_3$ and $R_4$ grouped together may constitute one or two fused carbon rings or heterocyclic rings, R represents an aryl group, a substituted aryl group, an aralkyl group, a substituted aralkyl group, an alkaryl group, a substituted alkaryl group, an alkenyl group or a substituted alkenyl group, and n is an integer of 1 or 2 or more.

3. A positive type light-sensitive composition as set forth in claim 2, wherein said composition further comprises a dye-borate complex represented by the following formula (II):

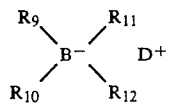 (II)

wherein $D^+$ represents a cation dye, and $R_9$, $R_{10}$, $R_{11}$ and $R_{12}$ each independently represents an alkyl group, a substituted alkyl group, an aryl group, a substituted aryl group, an aralkyl group, a substituted aralkyl group, an alkaryl group, a substituted alkaryl group, an alkenyl group, a substituted alkenyl group, an alicyclic group, a substituted alicyclic group or heterocyclic group.

4. A positive type light-sensitive composition as set forth in claim 1, wherein said composition further comprises a dye-borate complex represented by the following formula (II):

 (II)

wherein $D^+$ represents a cation dye, and $R_9$, $R_{10}$, $R_{11}$ and $R_{12}$ each independently represents an alkyl group, a substituted alkyl group, an aryl group, a substituted aryl group, an aralkyl group, a substituted aralkyl group, an alkaryl group, a substituted alkaryl group, an alkenyl group, a substituted alkenyl group, an alicyclic group, a substituted alicyclic group or heterocyclic group.

* * * * *